United States Patent [19]
Bhatnagar et al.

[11] Patent Number: 5,493,046
[45] Date of Patent: Feb. 20, 1996

[54] PROCESS

[75] Inventors: Neerja Bhatnagar, Savigny sur Orge; Jean Buendia, Le Perreux sur Marne; Christine Griffoul, Rosny Sous Bois, all of France

[73] Assignee: Roussel-Uclaf, France

[21] Appl. No.: 330,331

[22] Filed: Oct. 27, 1994

Related U.S. Application Data

[62] Division of Ser. No. 177,158, Jan. 4, 1994, Pat. No. 5,391,732.

[30] Foreign Application Priority Data

Sep. 16, 1993 [FR] France ................ 93 11030

[51] Int. Cl.⁶ .................................. C07D 231/10
[52] U.S. Cl. .................. 548/110; 546/13; 544/229; 549/213
[58] Field of Search .............. 548/110; 546/13; 544/229; 549/213; 540/467

[56] References Cited

PUBLICATIONS

CA 116:226995d Boronic . . . group. Nunn et al., p. 872, 1992.
CA 118:124607c Syntheses . . . tissue. Raju et al., p. 820, 1993.

*Primary Examiner*—Joseph K. McKane
*Attorney, Agent, or Firm*—Bierman and Muserlian

[57] ABSTRACT

The novel process of the invention for the preparation of a compound of the formula

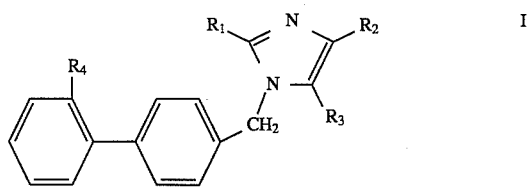

2 Claims, No Drawings

PROCESS

PRIOR APPLICATION

This application is a division of U.S. patent application Ser. No. 177,158 filed Jan. 4, 1994 now U.S. Pat. No. 5,391,732.

OBJECTS OF THE INVENTION

It is an object of the invention to provide a novel process for the preparation of a compound of formula I and novel intermediates.

This and other objects and advantages of the invention will become obvious from the following detailed description.

THE INVENTION

The novel process of the invention for the preparation of a compound of the formula wherein $R_1$ is selected from the group consisting of alkyl, alkenyl, alkynyl and alkylthio of up to 10 carbon atoms and cycloalkyl of 3 to 7 carbon atoms, all optionally substituted, $R_2$ and $R_3$ are individually selected from the group consisting of:

a) hydrogen, halogen —OH, —SH, acyl of an organic carboxylic acid of 1 to 7 carbon atoms, —$NO_2$, —CN, free, salified or esterified carboxy and —$PO_3(R)_2$, b) —$(CH_2)_{m1}$—$S(O)_{m2}$—X—$R_{10}$, c) alkyl, alkenyl, alkoxy and optionally oxidized alkylthio of up to 6 carbon atoms optionally interrupted by at least one —O—, —S— or nitrogen and optionally substituted, d) optionally substituted phenyl, benzoyl and optionally oxidized phenylthio, e)

—CO—N⟨$R_6$ / $R_7$⟩ or

—N⟨$R_8$ / $R_9$⟩ f) —S—S—$R_{12}$,

R is hydrogen or optionally substituted alkyl or phenyl, $m_1$ is an integer from 0 to 4, $m_2$ is an integer from 0 to 2, X is selected from the group consisting of a single bond, —NH—, —NHCO—, —NH—COO—, —N=CH—N—$R_{13}$ and —NHCONH—, $R_{10}$ and $R_{13}$ are individually selected from the group consisting of hydrogen, alkyl and alkenyl of up to 6 carbon atoms, cycloalkyl of 3 to 6 carbon atoms, optionally substituted phenyl and benzyl, pyridyl, nitropyridyl, pyrimidyl, tetrazolyl, diazolyl, piperidinyl, alkylpiperidinyl, thiazolyl, alkylthiazolyl, tetrahydrofuranyl and methyltetrahydrofuranyl; $R_6$ and $R_7$ or $R_8$ and $R_9$ are individually selected from the group consisting of hydrogen, amino acids, optionally substituted alkyl and alkenyl of up to 6 carbon atoms, optionally substituted phenyl, benzyl and phenethyl and —$(CH_2)_{m1}$—$S(O)_{m2}$—X—$R_{10}$ or $R_6$ and $R_7$ or $R_8$ and $R_9$ taken together with the nitrogen to which they are attached form a monocyclic ring of 5 to 7 ring members or condensed rings of 8 to 14 ring members, both optionally containing at least one heteroatom of the group consisting of —O—, —S— and nitrogen and optionally substituted with at least one member of the group consisting of halogen, —OH, —$NO_2$, alkyl and alkoxy of 1 to 6 carbon atoms, —$NH_2$, mono and dialkylamino of 1 to 6 carbon atoms and phenyl or $R_8$ and $R_9$ are individually acyl of an organic carboxylic acid of 1 to 6 carbon atoms or one of $R_8$ and $R_9$ is carbamoyl, alkoxylcarbonyl or benzyloxycarbonyl or $R_8$ and $R_9$ together with the nitrogen form phthalimido or succinimido, $R_{12}$ has the definitions of $R_2$ and $R_3$ except for amino or alkoxy with the proviso that at least one of $R_2$ and $R_3$ is an optionally substituted alkoxy or —$(CH_2)_{m1}$—$S(O)_{m2}$—X—$R_{10}$, $R_4$ is selected from the groups consisting of —$(CH_2)_{m1}$—$S(O)_{m2}$—X—$R_{10}$ as defined above, halogen, nitro, —$(CH_2)_{m1}$—$COOR_{14}$, —$(CH_2)_{m1}$—$CONHR_{14}$, —$(CH_2)_{m1}$—CN, in which ml has the meaning above, —$SO_2$—NH—$SO_2$—$R_{14}$, —NH—$SO_2$—$R_{14}$, —$PO_3R_{14}$, —NH—$SO_2CF_3$ and $$-SO_2-N-\overset{R_{13}}{\underset{|}{C}}-N(CH_3)_2,$$

—$(CH_2)_{m1}$—$SO_3R_{14}$, —CO—NH—$OR_{14}$, —CO—NH—NH—$SO_2$—$CF_3$, —CO—NH—$SO_2$—$R_{14}$, —$CH_2SO_2NHCO$—$R_{14}$, —$CH_2CONH$—$SO_2R_{14}$, —$NHSO_2NHCO$—$R_{14}$, —$NHCONHSO_2$—$R_{14}$, —$CONHSO_2NR_{14}R_{15}$, —$SO_2NHCONR_{14}R_{15}$, —$SO_2N(R_{14})OR_{15}$, —$SO_2NHPO(R_{14})_2$, —$CONHPO(R_{14})_2$, —$SO_2NHCN$, —$SO_2NHCOR_{14}$, —$SO_2NHSO_2NR_{14}R_{15}$, —$SO_2NHSO_2N(CH_2CH_2)_2Y$, —$NHSO_2NHSO_2R_{14}$, —$NHSO_2NHPO(R_{14})_2$, —$NR_{14}COCO_2H$, —$SO_2NHCO_2R_{14}$, in which $R_{13}$ has the definition above and $R_{14}$ and $R_{15}$ are individually selected from the group consisting of hydrogen, alkyl of 1 to 6 carbon atoms, optionally substituted cycloalkyl of 3 to 6 carbon atoms, and Y is oxygen or sulfur, all the alkyl, alkenyl, cycloalkyl, alkylthio, phenylthio, alkoxy, phenyl, benzyl radicals being optionally substituted by at least one member of the group consisting of halogen, hydroxyl, nitro, alkyl, alkenyl and alkoxy of up to 4 carbon atoms, trifluoromethyl, cyano, amino, mono and dialkylamino, free, salified or esterified carboxy, haloalkyl, alkylthio, haloalkylthio, haloalkoxy, phenyl, pyridyl, benzyl, phenethyl, benzoyl, phenoxy, benzyloxy, phenylthio, carbamoyl, acyl, acyloxy and tetrazolyl, the products of formula I being in all possible racemic, enantiomeric and diastereoismoeric isomer forms, as well as the addition salts with mineral and organic acids or with mineral and organic bases of the said products of formula I comprises reacting a compound of the formula in which $R'_1$, $R'_2$ and $R'_3$ have the meanings above for $R_1$, $R_2$ and $R_3$ respectively and in which the optional reactive functions are optionally protected with a compound of the formula:

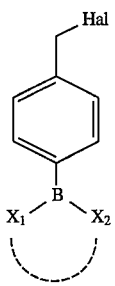   III in which Hal is halogen, B is boron and $X_1$ and $X_2$ are such that: either $X_1$ and $X_2$ are individually selected from the group consisting of hydroxyl, alkyl and alkoxy of 1 to 6 carbon atoms, phenyl and phenoxy, or $X_1$ with $X_2$ form with the boron atom to which they are linked a ring selected from the group consisting of

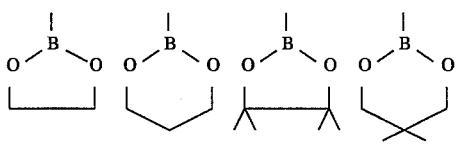

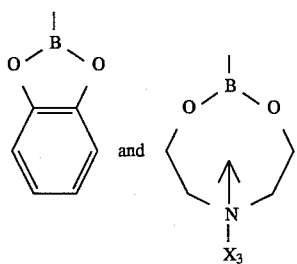

and $X_3$ is hydrogen or alkyl of 1 to 4 carbon atoms to obtain a product of the formula

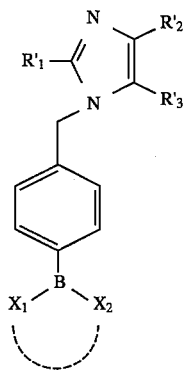   IV in which $R'_1$, $R'_2$, $R'_3$, $X_1$, $X_2$ and B have the meanings above, reacting the latter with a product of the formula

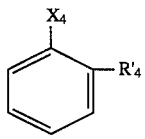   V in which $X_4$ is halogen, alkoxy, triflate or $-O-SO_2F$ and $R'_4$ has the meaning above for $R_4$ in which the optional reactive functions are optionally protected to obtain a product of the formula

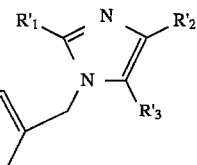   I' optionally subjecting the latter to one or more of the following reactions in any order:

a) an elimination reaction of the protective groups which can be carried by the protected reactive functions, b) a salification reaction with a mineral or organic acid or with a base, c) an esterification reaction of the acid function, d) a saponification reaction of the ester function, e) a conversion reaction of the cyano function into an acid function, f) a reduction reaction of the carboxy function into an alcohol function, g) a conversion reaction of the alkoxy function into the hydroxyl function, h) an oxidation reaction of the group containing a sulfur atom into a corresponding sulfoxide or sulfone function, i) a conversion reaction of the sulfoxide or sulfone function into a corresponding sulfoximine function, j) a conversion reaction of the nitrile into tetrazole, k) a resolution reaction of the racemic forms into resolved products, l) a conversion reaction of the carboxy into carbamoyl, m) a conversion reaction of the carbamoyl into nitrile, said products of formula I thus obtained being in all the possible racemic, enantiomeric and diastereoisomeric isomer forms.

In $-(CH_2)_{m1}-S(O)_{m2}-X-R_{10}$, when $m^1$ is other than 0, $-(CH_2)_{m1}-$ is alkylene such as methylene, ethylene, n-propylene or n-butylene and preferably when m is 0, 1 or 2, $-(CH_2)_{m1}$ is methylene, ethylene or a single bond. $-S(O)_{m2}-X-R_{10}$ moiety may be in a non-exhaustive manner selected from the group consisting of: $-SO_2-NH_2$, $-SO_2-NH-CH_3$, $-SO_2-NH-CF_3$, $-SO_2-NH-C_6H_5$, $-SO_2-NH-CH_2-C_6H_5$, $-CH_2-SO_2-NH_2$, $-CH_2-SO_2-NH-C_6H_5$, $-SO_2-NH-CO-NH-CH_3$, $-SO_2-NH-CO-NH-C_6H_5$, $-SO_2-NH-CO-NH-CF_3$, $-SO_2-NH-CO-NH-CH_2-C_6H_5$, $-SO_2-NH-CO-NH-D$ in which D is pyridine or pyrimidine,

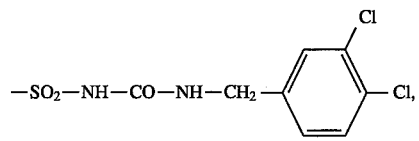

$-SO_2-NH-CO-NH-CH_2-CH_2-CH_3$, $-SO_2-NH-CO-NH-CH=CH-CH_3$,

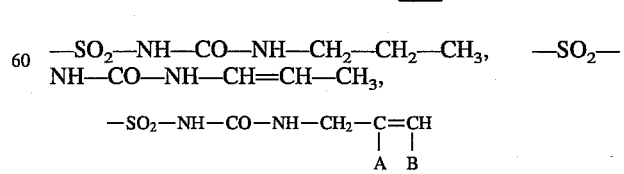

in which A and B are chosen from hydrogen, phenyl, pyridyl and pyrimidyl,

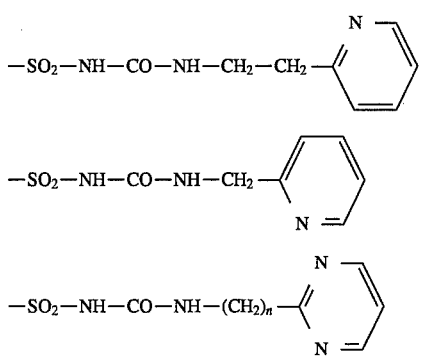

In the products of formula I and in what follows: the alkyl preferably designates methyl, ethyl, propyl, isopropyl, butyl isobutyl, sec.-butyl and tert-butyl but can also be pentyl or hexyl and particularly isopentyl and isohexyl. The term alkenyl preferably designates vinyl, allyl, 1-propenyl, butenyl and particularly 1-butenyl or pentenyl. The term alkynyl preferably designates ethynyl, propynyl and linear or branched butynyl.

Among the alkyls interrupted by one or more heteroatoms, there are methoxymethyl, methoxyethoxymethyl, propylthiopropyl, propyloxypropyl, propylthioethyl, methylthiomethyl. Halogen preferably designates chlorine or bromine, but can also be fluorine or iodine. The term alkoxy preferably designates methoxy, ethoxy, propoxy or isopropoxy, but can also be n- or secondary or tertiary butoxy.

The acyl preferably is derived from an organic carboxylic acid of 1 to 6 carbon atoms such as formyl, acetyl, propionyl, butyryl or benzoyl, but also pentanoyl, hexanoyl, acryloxyl, crotonoyl or carbamoyl. The amino substituted by one or two alkyls preferably designates groups in which the alkyl is chosen from the alkyls defined above such as for monoalkyl amino, methylamino or ethylamino, or for dialkylamino dimethylamino or methylethylamino. Acyloxy designates an acyl with the values indicated above and preferably formyloxy, acetyloxy, propionyloxy, butyryloxy or benzoyloxy. Cycloalkyl preferably designates cyclopropyl, cyclobutyl, cyclopentyl or cyclohexyl.

The monocyclic and condensed rings designate saturated or unsaturated rings. Examples of saturated monocyclic are pyrrolidinyl, imidazolidinyl, pyrazolidinyl, piperidyl, piperazinyl, morpholinyl, thio-morpholinyl, azepinyl, or unsaturated monocycles such as: pyrannyl, pyrrolyl, imidazolyl, pyrazolyl, pyridyl, pyrazinyl, pyrimidinyl, pyridazinyl, thiazolyl, thiadiazolyl, oxazolyl, furazannyl, pyrrolinyl such as delta 2-pyrrolinyl, imidazolinyl such as delta 2-imidazolinyl, pyrazolinyl such as delta 3-pyrazolinyl as well as the position isomers of the heteroatom or heteroatoms which these groups can contain such as isothiazolyl or isoxazolyl.

The condensed rings may be saturated such as 1-oxa spiro [4,5]decyl, tetrahydropyran-2-spirocyclohexyl, cyclohexanespiro-2'-(tetrahydrofuran) or 1, 10-diaza anthr-4-yl, or unsaturated such as benzothienyl, naphtho[2,3-b]thienyl, idenyl, indolizinyl, isoindolyl, 3H-indolyl, indolyl, indazolyl, purinyl, quinolizinyl, benzopyrrolyl, benzimidazolyl, isoquinolyl, quinolyl, phthalazinyl, naphthyridinyl, quinoxalinyl, quinazolinyl, cinnolinyl, pteridinyl, carbazolyl, beta-carbolinyl, acridinyl, phenazinyl, indolinyl, isoindolinyl and also condensed polycyclic systems constituted by heterocyclic monocycles as defined above such as furo[2,3-b]pyrrole or thieno[2,3-b]furan.

Haloalkyl is the alkyl as defined above and is substituted by one or more halogens as defined above for example bromoethyl, trifluoromethyl, trifluoroethyl or pentafluoroethyl. Alkylthio preferably is the alkyl as defined above, for example methylthio or ethylthio and haloalkylthio preferably is the alkyl as defined above and is substituted by one or more halogens as defined above, for example bromoethylthio, trifluoromethylthio, trifluoroethylthio or pentafluoroethylthio. Haloalkoxythio preferably is the alkoxy as defined above and is substituted by one or more halogens as defined above, for example bromoethoxy, trifluoromethoxy, trifluoroethoxy or pentafluoro-ethoxy.

Carbamoyl also designates carbamoyl substituted by a lower N-monoalkyl carbamoyl such as N-methylcarbamoyl, N-ethylcarbamoyl, a lower N,N-dialkyl carbamoyl such as N,N-dimethylcarbamoyl, N,N-diethylcarbamoyl; and N-(lower hydroxyalkyl) carbamoyl such as N-(hydroxymethyl) carbamoyl, N-(hydroxyethyl) carbamoyl, a lower carbamoylalkyl such as carbamoylmethyl and carbamoylethyl. Phenyl substituted by an alkythio is for example benzylthio.

In the products of formula I and in what follows, the alkyl, alkenyl, cycloalkyl and phenyl which can be represented by or carried by $R_1$, $R_2$, $R_3$ and $R_4$ can take the values defined above and may or may not be substituted by one or more identical or different substituents as defined above. Therefore, $R_2$ and $R_3$ can, for example, be alkylthio, phenylthio, alkylsulfinyl phenylsulfinyl, alkylsufonyl or arylsufonyl but also cycloalkylthio such as cyclohexylthio. Alkylthio, alkylsulfinyl and alkylsulfonyl may be linear or branched alkyl as indicated above for the alkyl. Examples are methylthio, hydroxymethylthio, ethylthio, aminoethylthio, methylsulfinyl, ethylsulfinyl, methylsulfonyl, ethylsulfonyl, propylthio, isopropylthio, butylthio, sec-butylthio, tert-butylthio, isopentylthio or isohexylthio or those in which the thio is oxidized into the sulfinyl or sulfonyl.

Depending on the values of m1, m2 and $R_{10}$ in $-(CH_2)_{m1}-S(O)_{m2}-X-R_{10}$, $R_2$ and $R_3$ can also be phenylthio, pyridylthio or pyrimidylthio, imidazolylthio, N-methylimidazolylthio as well as those in which the thio is oxidized into the sulfinyl or sulfonyl such as phenylsulfinyl or phenylsulfonyl.

As examples of substituted alkyls, there are those substituted by one or more phenyl for example, benzyl, diphenylmethyl and triphenylmethyl, and those substituted by pyridyl, for example pyridylmethyl, it being understood that in the non-exhaustive list of examples as mentioned above, the alkyl can also just as equally be ethyl, propyl or butyl such as phenethyl.

Examples of substituted alkenyl are those substituted with at least one phenyl or pyridyl, as indicated in the examples given above in which the alkyl is replaced by an alkenyl for example phenylvinyl or phenylallyl.

The carbamoyl and amino radicals mentioned above in particular:

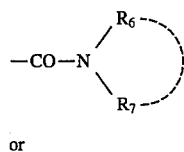

or

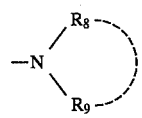

designate groups in which two identical or different groups are linked to the nitrogen atom selected from the group consisting of hydrogen to obtain the amino; the alkyl as defined above to obtain the monoalkyl- or dialkylamino in which the linear or branched alkyl have 1 to 6 carbon atoms and particularly methyl, ethyl, isopropyl, methoxymethyl, methoxyethyl or ethoxyethyl; phenyl, benzyl, phenethyl optionally substituted to obtain the phenylamino or benzylamino.

Among the substituted carbamoyl, there are lower N-monoalkyl carbamoyl, for example, N-methylcarbamoyl, N-ethylcarbamoyl; the lower N,N-dialkyl carbamoyl, for example, N,N-dimethylcarbamoyl, N,N-diethylcarbamoyl; the N-(lower hydroxyalkyl) carbamoyl, for example, N-(hydroxymethyl) carbamoyl, N-(hydroxyethyl) carbamoyl; the lower carbamoylalkyl, for example carbamoylmethyl, carbamoylethyl; phenylcarbamoyl; pyridylcarbamoyl; benzylcarbamoyl; N-methyl N-phenylcarbamoyl; pyridylmethylcarbamoyl.

The expression amino acid is preferably a remainder derived from one of the natural amino acids such as glycine, alanine, valine, leucine, isoleucine, phenylalanine and particularly proline or one of the other natural amino acids known to one skilled in the art.

Among the $-(CH_2)_{m1}-X-R_{10}$ which can be represented by $R_6$, $R_7$, $R_8$ or $R_9$ are $-NH-SO_2-CH_3$, $-NH-SO_2-C_6H_5$, $-NH-SO_2-CF_3$, $-NH-CH_2-SO_2-NH-C_6H_5$, $-CO-NH-SO_2-C_2H_5$, $-CO-NH-SO_2-CH_3$, $-CO-NH-SO_2-CH_2-C_6H_5$. The heterocycle which can be formed with $R_6$ and $R_7$ or $R_8$ and $R_9$ is preferably saturated.

It can be optionally substituted by the substituents already mentioned previously and particularly by one or more members selected from the group consisting of chlorine, fluorine, methyl, ethyl, isopropyl, tert-butyl, methoxy, ethoxy, propoxy, benzoyl, methoxycarbonyl, ethoxycarbonyl. For example methylpiperazinyl, ethylpiperazinyl, propylpiperazinyl, phenyl-piperazinyl or benzylpiperazinyl. In these last two, the phenyl and benzyl can be substituted as indicated previously for example chlorophenyl or trifluorophenyl.

The acyl of $R_8$ and $R_9$ can be chosen from acetyl, propionyl, butyryl, pentanoyl and carbamoyl. When $R_8$ or $R_9$ is alkoxy-carbonyl, this is preferably tert-butyloxycarbonyl.

The carboxy of the products of formula I can be salified or esterified by various groups known to one skilled in the art among which there can be mentioned, for example: among the salification compounds, mineral bases such as sodium, potassium, lithium, calcium, magnesium or ammonium salt or organic bases such as methylamine, propylamine, trimethylamine, diethylamine, triethylamine, N, N-dimethylthanolamine, tris (hydroxymethyl) amino methane, ethanolamine, pyridine, picoline, dicyclo-hexylamine, morpholine, benzylamine, procaine, lysine, arginine, histidine, N-methylglucamine.

Among the esterification compounds are, alkyl to form alkoxy carbonyl groups such as methoxycarbonyl, ethoxycarbonyl, tertbutoxycarbonyl or benzyloxycarbonyl which alkyls may be substituted by members selected from the group consisting of halogen, hydroxyl, alkoxy, acyl, acyloxy, alkylthio, amino or aryl such as chloromethyl, hydroxypropyl, methoxymethyl, propionyloxymethyl, methylthiomethyl, dimethylaminoethyl, benzyl or phenethyl.

The addition salts with mineral or organic acids of the products of formula I can be the salts formed with the following acids: hydrochloric acid, hydrobromic acid, hydroiodic acid, nitric acid, sulfuric acid, phosphoric acid, propionic acid, acetic acid, formic acid, benzoic acid, maleic acid, fumaric acid, succinic acid, tartaric acid, citric acid, oxalic acid, glyoxylic acid, aspartic acid, ascorbic acid, alkylmonosulphonic acid such as methanesulfonic acid, ethanesulfonic acid, propanesulfonic acid, alkyldisulfonic acid such as methanedisulfonic acid, α,β-ethanedisulfonic acid, arylmonosulfonic acid such as benzenesulfonic acid and aryldisulfonic acid.

When $R_2$ and $R_3$ both are individually an optionally oxidized sulfurous alkylthio or phenylthio, the preferred products of the invention are particularly the products of formula I in which these sulphurous groups have the same degree of oxidation.

Among the preferred compounds of formula I are those wherein one of $R_2$ and $R_3$ is an optionally oxidized sulfur group as defined above and the other is alkyl, alkoxy, free, salified or esterifed carboxy or optionally substituted phenyl, preferably $R_2$.

$R_2$ and/or $R_3$ can be notably alkylthio or alkenylthio optionally substituted by one or more formyl; hydroxyl; alkoxy; acyloxy; free, salified or esterified carboxy; amino; substituted amino; carbamoyl; substituted carbamoyl; alkylthio; phenylthio; pyridinyl; pyrimidinyl; phenyl.

Among the substituents which can be carried by $R_2$ and $R_3$ amino and carbamoyl can in particular be substituted by one or two alkyl and amino acids mentioned above.

The substituted amino and carbamoyl which can be carried by $R_2$ and $R_3$ can also form a heterocycle such as those mentioned above.

Also $R_2$ and $R_3$ can be notably alkylthio substituted by one or more halogen atoms such as chlorine and fluorine. For example the following can be mentioned: $-S-CF_3$; $-S-CHF_2$; $-S-CH_2F$; $-S-CF_2-CHF_2$; $-S-CF_2-CHFCl$.

$R_2$ and $R_3$ can thus represent:

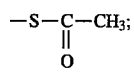

$-SO_3H$; $-S-CH_3$; $-S-(CH_2)_{n1}-S-(CH_2)_{n2}-X_4$; $-S-(CH_2)_n-X_4$; $-S-(CH_2)_{n1}-NH-(CH_2)_{n2}-X_4$; $-S-CH=CH-(CH_2)_n-X_4$; $-S-(CH_2)_{n1}-CH=CH-(CH_2)_{n2}-X_4$; in which $X_4$ is H, OH, cyclohexyl, pyridyl, phenyl, CHO, COOH, $NH_2$ or

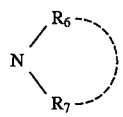

and n, $n_1$ and $n_2$ individually represent 0, 1 or 2.

$R_2$ and $R_3$ can be particularly $-COOH$; $-CO_2X_5$; $-SX_5$; $-NH_2$; $-C\equiv N$; $-OMe$; $-OEt$; $-CH=CH-COOH$; tetrazolyl;

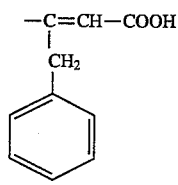

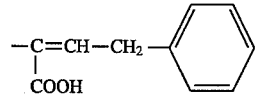

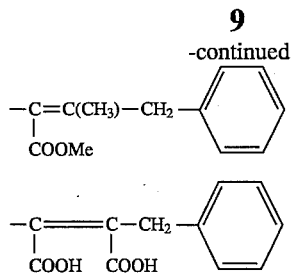

in all their isomer, cis-trans isomer forms,

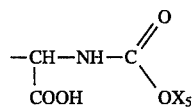

—NH—CH$_2$—COO—X$_5$ —NH—COO—X$_5$ X$_5$ is alkyl or aryl.

R$_2$ and R$_3$ can preferably be

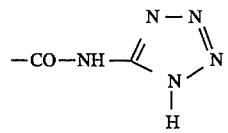

The products of formula I represent in particular products in which R$_2$ and R$_3$ have the meanings indicated above and quite particularly products in which R$_2$ is an optionally substituted alkylthio as defined above or an alkoxy such as methoxy and R$_3$ is a free, salified or esterified carboxy or an amidified carboxy such as —COOH, —COO methyl, —COO-ethyl, —CONH$_2$ or

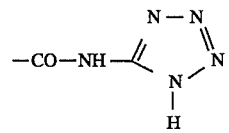

Among the preferred values of R$_4$ are cyano, —(CH$_2$)$_{m1}$—SO$_2$—X—R$_{10}$ as defined above and more particularly —SO$_2$—NH—CO—NH—CH$_2$—CH=CH$_2$, —SO$_2$—NH—CO—NH—CH$_2$—CH$_2$—CH$_3$, —SO$_2$—N$^-$—CO—NH—CH$_2$—CH$_2$—CH$_3$, K$^+$

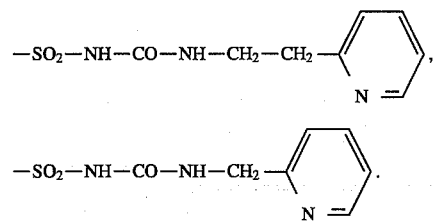

The invention is preferably the above process for the preparation of products of the formula

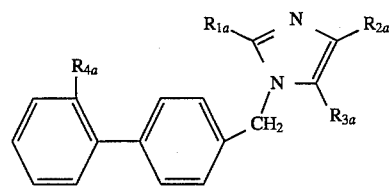

in which:

R$_{1a}$ is alkyl or alkenyl of up to 4 carbon atoms,

R$_{2a}$ and R$_{3a}$ are individually chosen from:

a) hydrogen, mercapto; formyl; free, salified or esterified carboxy; halogen; hydroxyl; cyano; nitro; acyl;

b) alkyl, alkenyl, alkoxy, alkylthio in which the sulfur atom is optionally mono- or dioxidized having up to 6 carbon atoms, phenyl, benzoyl, phenylthio in which the sulfur atom is optionally mono- or dioxidized, all being optionally substituted by at least one member of the group consisting of halogen, hydroxyl, trifluoromethyl, cyano, nitro, formyl, alkyl and alkoxy of 1 to 4 carbon atoms, phenyl and free, salified or esterified carboxy, C) 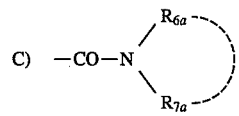

and

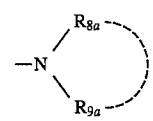

in which:

either R$_{6a}$, R$_{7a}$, R$_{8a}$ and R$_{9a}$ are individually chosen from hydrogen, amino acids, alkyl of 1 to 6 carbon atoms, phenyl, benzyl, phenethyl or R$_{6a}$ and R$_{7a}$ and R$_{8a}$ and R$_{9a}$ form respectively with the nitrogen atom to which they are linked a heterocyclic selected from the group consisting of imidazolyl, pyrrolyl, pyrrolinyl, pyrrolidinyl, pyridyl, piperidinyl, pyrimidinyl, pyridazinyl, pyrazinyl, piperazinyl, phenylpiperazinyl, piperidyl, oxazolyl, morpholinyl and thiomorpholinyl, azepinyl, indolyl, optionally substituted by at least one member of the group consisting of halogen, hydroxyl, nitro, alkyl and alkoxy of 1 to 6 carbon atoms and phenyl, R$_{4a}$ is cyano, free, salified or esterified carboxy, —(CH$_2$)$_p$—X$_a$—R$_{10a}$ in which p is 0 or 1, X$_a$ is —NH—, —NH—CO—, —NH—CO—O—, —N=CH—N—R$_{13a}$, —NH—CO—NH— or a single bond and R$_{10a}$ and R$_{13a}$ are individually selected from the group consisting of alkyl or alkenyl of up to 6 carbon atoms and optionally substituted, pyridyl, phenyl, benzyl, nitropyridyl, pyrimidyl, tetrazolyl, diazolyl, piperidinyl, alkylpiperidinyl, thiazolyl, alkylthiazolyl, tetrahydrofuranyl and methyltetrahydrofuranyl; the alkyl and alkenyl being optionally substituted by at least one member of the group consisting of halogen, hydroxyl, nitro, alkyl, alkenyl and alkoxy of up to 4 carbon atoms, trifluoromethyl, cyano, amino, mono- and dialkylamino, free, salified or esterified carboxy, phenyl and tetrazolyl; the said products of formula I$_a$ being in all possible racemic, enantiomeric and diastereoisomeric isomer forms, as well as the addition salts with mineral and organic acids or with mineral and organic bases of the said products of formula I$_a$, characterized in that for their preparation as defined above, products of formulae A, II, III and a reagent capable of introducing the R'$_2$ radical are used in which R'$_1$, R'$_2$, R'$_3$ and R'$_4$ have the values indicated above for R$_{1a}$, R$_{2a}$, R$_{3a}$ and R$_{4a}$ respectively in which the reactive functions are optionally protected.

Another preferred process of the invention for the preparation of compounds of the formula

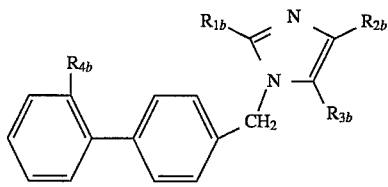

in which:

$R_{1b}$ is alkyl of up to 1 to 4 carbon atoms, $R_{3b}$ is hydrogen, formyl, acyloxy, alkyl or alkoxy optionally substituted or carboxy free, salified or esterified by an alkyl, $R_{2b}$ is optionally substituted phenylthio, phenylsulfonyl, phenylsulfinyl, alkylthio, alkylsulfonyl or alkylsulfinyl such as in all those represented by $R_{2b}$ and $R_{3b}$, alkyl and alkoxy of 1 to 6 carbon atoms, and the phenyl is optionally substituted by one or more groups chosen from halogen, hydroxyl, trifluoromethyl, acyloxy, free salified or esterified carboxy, phenyl, pyridyl, tetrazolyl, alkyl and alkoxy of 1 to 4 carbon atoms optionally substituted by alkoxy of 1 to 4 carbon atoms, $R_{4b}$ is cyano, free, salified or esterified carboxy, $—SO_2—X_b—R_{10b}$ in which $X_b$ is $—NH—$, $—NH—CO—$, $—NH—CO—O—$,

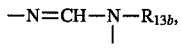

$—NH—CO—NH—$ or a single bond and $R_{10b}$ and $R_{13b}$ are individually selected from the group consisting of hydrogen, methyl, ethyl, propyl, vinyl, allyl, pyridyl, phenyl, benzyl, nitropyridyl, pyrimidyl, tetrazolyl, diazolyl, piperidinyl, alkylpiperidinyl, thiazolyl, alkylthiazolyl, tetrahydrofuranyl and methyltetrahydrofuranyl, the said products of formula $I_b$, being in all possible racemic, enantiomeric and diastereoisomeric isomer forms, as well as the addition salts with mineral and organic acids or with mineral and organic bases of said products of formula $I_b$, characterized in that for their preparation as defined above, products of formulae A, II, III and a reagent capable of introducing $R'_2$ are used in which $R'_1$, $R'_2$, $R'_3$ and $R'_4$ have the values indicated above for $R_{1b}$, $R_{2b}$, $R_{3b}$ and $R_{4b}$ respectively in which the reactive functions are optionally protected.

A more particular subject of the invention is the process for the preparation of products of the formula

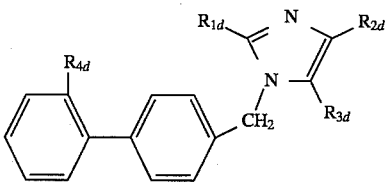

in which:

$R_{1d}$ is alkyl of 1 to 4 carbon atoms, $R_{3d}$ is selected from the group consisting of carboxy free, salified or esterified by alkyl of 1 to 4 carbon atoms, formyl, acyloxy, alkyl of 1 to 4 carbon atoms optionally substituted by hydroxyl, $R_{2d}$ is selected from the group consisting of phenylthio, phenylsulfonyl, phenylsulfinyl, alkylthio, alkylsulfonyl or alkylsulfinyl, in which the alkyl has 1 to 4 carbon atoms, and $R_{4d}$ is $—SO_2—NH_2$, $—SO_2—NH—CO—O—R_{10d}$, $—SO_2—N=CH—NR_{13d}$, or $—SO_2—NH—CO—NH—R_{10d}$ in which $R_{10d}$ and $R_{13d}$ are individually selected from the group consisting of hydrogen, methyl, ethyl, n-propyl and propenyl, the said products of formula $I_d$ being in all possible racemic, enantiomeric and diastereoisomeric isomer forms, as well as the addition salts with mineral and organic acids or with mineral and organic bases of said products of formula $I_d$, characterized in that for their preparation as defined above, products of formulae II, III and IV and a reagent capable of introducing the $R'_2$ are used in which $R'_1$, $R'_2$, $R'_3$ and $R'_4$ have the values indicated above for $R_{1d}$, $R_{2d}$, $R_{3d}$ and $R_{4d}$ respectively in which the reactive functions are optionally protected.

In a preferred mode of the process, the compound of formula II with $R'_1$ being alkyl of 1 to 4 carbon atoms, $R'_3$ is selected from the group consisting of free, salified or esterified carboxy with alkyl of 1 to 4 carbon atoms formyl, acyloxy and alkyl of 1 to 4 carbon atoms optionally substituted with hydroxy and $R'_2$ is selected from the group consisting of phenylthio, phenylsulfonyl, phenylsulfinyl, alkylthio, alkylsulfonyl and alkylsulfinyl of 1 to 4 alkyl carbon atoms and the protective groups are optionally protected is reacted with a compound of formula V wherein $R'_4$ is selected from the group consisting of $—SO_2—NH_2$, $—SO_2—NH—CO—O—R_{10d}$, $—SO_2—N=CH—NR_{13d}$, or $—SO_2—NH—CO—NH—R_{10d}$ in which $R_{10d}$ and $R_{13d}$ are individually chosen from hydrogen, methyl, ethyl, n-propyl and propenyl, in which the reactive functions are optionally protected.

More preferably, the compound of formula II has $R'_3$ as alkoxy or free, salified or esterified carboxy and $R'_2$ is alkylthio or phenylthio optionally oxidized in the form of the sulfoxide or sulfone, these alkoxy, alkylthio and phenylthio being optionally substituted by at least one member of the group consisting of halogen, alkyl and alkoxy of 1 to 4 carbon atoms, trifluoromethyl, amino, mono or dialkylamino, cyano, acyl, acyloxy and phenyl.

The compounds of formula I preferred by the process are preferably

- 2-butyl-1-[[2'-carboxy-(1,1'-biphenyl)-4-yl]-methyl]-4-(phenylthio)-1H-imidazole-5-carboxylic acid,
- 2-butyl-1-[[2'-carboxy-(1,1'-biphenyl)-4-yl]-methyl]-4-(methylthio)-1H-imidazole-5-carboxylic acid,
- 4'-[[2-butyl-4-(ethylthio)-5-(hydroxymethyl)-1H-imidazol-1-yl]-methyl]-(1,1'-biphenyl)-2-carboxylic acid,
- 2-butyl-1-[[2'-carboxy-(1,1'-biphenyl)-4-yl]-methyl]-4-(ethylsulfonyl)-1H-imidazole-5-carboxylic acid,
- 2-butyl-1-[[2'-carboxy-(1,1'-biphenyl)-4-yl]-methyl]-4-(ethylsulfinyl)-1H-imidazole-5-carboxylic acid,
- 2-butyl-1-[[2'-carboxy-(1,1'-biphenyl)-4-yl]-methyl]-4-(ethylthio)-1H-imidazole-5-carboxylic acid,
- 2-butyl-1-[[2'-carboxy-(1,1'-biphenyl)-4-yl]-methyl]-4-(phenylsulfonyl)-1H-imidazole-5-carboxylic acid,
- 2-butyl-1-[[2'-carboxy-(1,1'-biphenyl)-4-yl]-methyl]-4-(phenylsulfinyl)-1H-imidazole-5-carboxylic acid,
- 2-butyl-1-[[2'-tetrazolyl-(1,1'-biphenyl)-4-yl]-methyl]-4-(methylthio)-1H-imidazole-5-carboxylic acid,
- -ethyl 2-butyl-4-(methylthio)-1-[[2'-((((propylamino)-carbonyl)-amino)-sulfonyl)-(1,1'-biphenyl)-4-yl]-methyl]-1H-imidazole-5-carboxylate,
- 2-butyl-4-(methylthio)-1-[[2'-((((propylamino)-carbonyl)-amino)-sulfonyl)-(1,1'-biphenyl)-4-yl]-methyl]-1H-imidazole-5-carboxylic acid,
- 2-butyl-4-(methylthio)-1-[[2'-((((propylamino)-carbonyl)-amino)-sulfonyl)-(1,1'-biphenyl)-4-yl]-methyl]-1H-imidazole-5-carboxylic acid, -di-potassium salt, Preferably, the compound of formula III is such that Hal is preferably bromine but can also be chlorine or iodine.

The reaction of the product of formula III with the product of formula II can be carried out in a solvent such as dimethylformamide, tetrahydrofuran, acetone, acetonitrile, dimethylpropylurea, dimethoxyethane or dimethylsulfoxide at reflux of the solvent or at ambient temperature, preferably with stirring. The reaction is carried out in the presence of a base such as sodium or potassium hydride, sodium or potassium methylate, ethylate or tert-butylate, or preferably, sodium, potassium or caesium carbonate.

The reaction of the product of formula IV with the compound of formula V as defined above in which $X_4$ is preferably bromine, iodine or chlorine can be carried out in a solvent such as a mixture of toluene and ethanol or dimethylformamide in the presence of a weak base such as sodium, potassium or caesium bicarbonate, preferably in the presence of a catalyst such as tetrakis triphenylphosphine palladium or a mixture of triphenylphosphine and palladium diacetate or also in tetrakis triphenylphosphine nickel.

As other catalysts, there can be mentioned nickel, Pd, Rh or Pt complexes and preferably complexes of palladium; bis(dibenzylidene acetone) Pd in the presence of $PPh_3$; tris(dibenzylidene acetone) Pd; trans-benzyl (chloro) bis-(triphenylphosphine) palladium; $Pd(OAc)_2$ tris furyl phosphine; $Pd(OAc)_2$ triphenyl phosphine; tetrakis triphenylphosphine palladium; 1,4 bis(diphenylphosphino) butane Pd, Cl, Br or OAc; 1,3 bis(diphenyl phosphino) propane Pd, Cl, Br or OAc; 1,2 bis(diphenyl phosphino) ethane Pd, Cl, Br or OAc; 1,1 bis(diphenyl phosphino) ferrocene Pd, Cl, Br, or OAc.

In the reaction of the product of formula IV with the product of formula V, the solvents used are preferably degassed beforehand, for example by bubbling argon through them.

The various reactive functions that can be carried by certain compounds of the reactions defined above can, if necessary, be protected. They can be for example hydroxyl, acyl, free carboxy or also amino and monoalkylamino which can be protected by appropriate protective groups. A list of the different protective groups which can be used will be found for example in the French Patent No. 2,499,995.

The following non-exhaustive list of examples of the protection of the reactive functions can be mentioned: the hydroxyl groups can be protected for example by alkyl such as tert-butyl, trimethylsilyl, tert-butyldimethylsilyl, methoxymethyl, tetrahydropyrannyl, benzyl or acetyl. The amino groups can be protected for example by acetyl, trityl, benzyl, tert-butoxycarbonyl, phthalimido or by others known in the chemistry of the peptides. Acyl groups such as formyl can be protected in the form of cyclic or non-cyclic ketals such as dimethyl- or diethylketal or ethylene dioxyketal and the acid functions of the products can be optionally amidified by a primary or secondary amine for example in methylene chloride in the presence of 1-ethyl-3-(dimethylaminopropyl)-carbodiimide hydrochloride at ambient temperature. The acid functions can be protected for example in the form of esters formed with easily-cleavable esters such as benzyl or ter-butyl esters or esters known in the chemistry of the peptides.

Depending upon the values of $R'_1$, $R'_2$, $R'_3$ and $R'_4$, the products of formula I' as defined above constitute or do not constitute products of formula I.

The reactions to which the products of formula I' as defined above can be optionally subjected, can be carried out, for example, as indicated below to obtain the compounds of formula I.

The elimination of the protective groups such as those indicated above can be carried out under the usual conditions known to one skilled in the art, particularly by an acid hydrolysis carried out with an acid such as hydrochloric acid, benzene sulfonic acid or para-toluene sulfonic acid, formic acid or trifluoroacetic acid or also by catalytic hydrogenation. The phthalimido group can be eliminated with hydrazine.

The products described above can, if desired, be subjected to salification reactions for example with a mineral or organic acid according to the usual methods known to one skilled in the art. The products described above can, if desired, be subjected, on the optional carboxy functions, to salification reactions with a mineral or organic base or esterification reactions. These esterification and salification reactions can be carried out according to the usual methods known to one skilled in the art.

The optional conversions of the ester functions into the acid function of the products described above can be, if desired, carried out under the usual conditions known to one skilled in the art, particularly alkaline or acid hydrolysis for example with sodium hydroxide or potassium hydroxide in an alcoholic medium such as in methanol or with hydrochloric acid or sulfuric acid.

The optional cyano functions of the products can be, if desired, converted into an acid function by the usual conditions known to one skilled in the art, for example by a double hydrolysis carried out in an acid medium such as in a sulfuric acid, glacial acetic acid and water mixture, these three compounds preferably being in equal proportions, or in a sodium hydroxide, ethanol and water mixture under reflux.

The optional free or esterified carboxy functions of the products can be, if desired, reduced into an alcohol function by methods known to one skilled in the art. For the esterified carboxy functions, lithium aluminium hydride can be used in a solvent such as tetrahydrofuran or dioxane or ethyl ether. For the free carboxy functions, boron hydride can be used.

The optional alkoxy functions such as methoxy of the products can be, if desired, converted into a hydroxyl function under the usual conditions known to one skilled in the art, for example with boron tribromide in a solvent such as methylene chloride, with pyridine hydrobromide or hydrochloride or with hydrobromic acid or hydrochloric acid in water or with acetic acid under reflux.

The optional groups containing a sulfur atom of the products can be, if desired, converted into the corresponding sulfoxide or sulfone function under the usual conditions known to one skilled in the art such as by means of peracids such as peracetic acid or methachloroperbenzoic acid or with ozone, oxone, sodium periodate in a solvent such as methylene chloride or dioxane at ambient temperature.

The sulfoxide function can be obtained with an equimolar mixture of the product containing an alkylthio or arylthio and of the reagent such as a peracid. The sulfone function can be obtained with a mixture of the product containing an alkylthio or arylthio with an excess of reagent such as a peracid.

The optional alcohol function of the products can be, if desired, converted into the aldehyde or acid function by oxidation under the usual conditions known to one skilled in the art such as by the action of manganese oxide to obtain aldehydes or Jones reagent to obtain acids.

The optional nitrile functions of the products can be, if desired, converted into tetrazole in the usual conditions known to one skilled in the art such as by the cycloadditon of a metal azide such as a trialkyltin azide on the nitrile function as indicated in the method described in KOZIMA et al, J. Organometallic Chemistry, Vol. 33, p. 337, (1971).

The optional optically active forms of the products of formula I can be prepared by resolution of the racemics according to the usual methods known to one skilled in the art. The conversion reactions of the formyl into the carbamoyl and of the carbamoyl into the nitrile are carried out according to the usual conditions known to one skilled in the art.

The products of formula I are known and are described in European Patent Application No. 0,465,368 and No. 0,503,162. The products of formula I prepared by the process as defined above, as well as their addition salts with acids, have useful pharmacological properties. They are endowed with antagonistic properties for the angiotensin II receptor and are particularly inhibitors of the effects of angiotensin II, especially of the vasoconstrictive effect and also of the trophic effect at the level of the myocytes.

These properties justify the use in therapeutics of the products of formula I prepared according to the process as defined above as medicaments, and are useful in the treatment of arterial hypertension, cardiac insufficiencies, renal insufficiencies and in the prevention of the post-angioplastic recurrence of stenosis. They can also be used in the treatment of certain gastrointestinal, gynaecological disorders and particularly for a relaxing effect at the level of the uterus.

The compositions can be administered orally, rectally, parenterally or locally as a topical application on the skin and mucous membranes. The compositions can be solid or liquid and in the forms of tablets, dragees, capsules, granules, suppositories, injectable preparations, ointments, creams, gels and aerosol preparations prepared by the usual methods. The active ingredient can be incorporated with excipients usually employed in these pharmaceutical compositions such as talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, preservatives.

The usual dose, variable according to the product used, the patient treated and the illness in question, can be from 1 to 100 mg per day in an adult, by oral route.

Some of the starting products of formula II are known and can be prepared as indicated in European Patent EP 168,950. The starting products of formula II can be prepared by reacting a compound of the formula

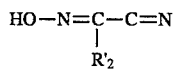   II$_a$ in which R'$_2$ has the the meaning above with a reducing agent to obtain a corresponding amine of the formula

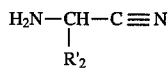   II$_b$ in which R'$_2$ has the above meaning, reacting the latter with a compound of the formula

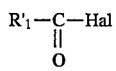   II$_c$ in which R'$_1$ has the meaning above, and Hal is halogen to obtain a product of the formula

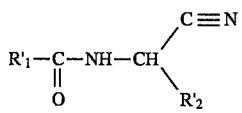   II$_d$ in which R'$_1$ and R'$_2$ have the above meanings, reacting the latter with the compound of the formula

   II$_e$ in which R'$_3$ has the above meaning, and Y is sulfur or oxygen to obtain a product of the formula

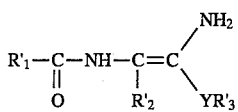   IIf in which R'$_1$, R'$_2$, R'$_3$ and Y have the above meanings, subjecting the latter to a cyclization reaction to obtain a product of formula II which is optionally subjected to one or more of the following reactions, in any order:

a) an elimination reaction of the protective groups which can be carried by the protected reactive functions, b) a salification reaction with a mineral or organic acid or with a base to obtain the corresponding salt, c) an esterification reaction of the acid function, d) a saponification reaction of the ester function into an acid function, e) a conversion reaction of the cyano function into an acid function, f) a reduction reaction of the carboxy function into an alcohol function, g) a conversion reaction of the alkoxy function into a hydroxyl function, h) an oxidation reaction of the group containing a sulfur atom into a corresponding sulfoxide or sulfone function, i) an oxidation reaction of the alcohol function into an aldehyde or acid function, j) a conversion reaction of the nitrile function into tetrazole, k) a resolution reaction of the racemic forms into resolved products, l) a conversion reaction of the carboxy into the carbamoyl, m) a conversion reaction of the carbamoyl into a nitrile, the said products of formula II thus obtained being in all possible racemic, enantiomeric and diastereoisomeric isomer forms.

In the preferred conditions for implementing the invention, the above process is carried out in the following manner: the reduction of the oxime of formula II$_a$ can be carried out by the usual methods known to one skilled in the art such as with an aluminium amalgam prepared under the usual conditions such as by the action of mercury chloride on aluminium. The reaction is carried out in a solvent such as tetrahydrofuran or toluene, preferably at a temperature of approximately 50° C.

The addition of the product of formula II$_c$ in which W is bromine or preferably chlorine on the amine of formula II$_b$ can be carried out by methods known to one skilled in the art, for example in the presence of a base such as pyridine or triethylamine and the reaction is preferably carried out at a temperature of approximately 0° C.

The compound of formula II$_d$ can also be obtained by subjecting the compound of formula II$_a$ to a reduction and acylation reaction in the presence of an anhydride such as acetic, butyric or valeric anhydride, by hydrogenation in the presence of palladium or zinc or of sodium dithionite.

The addition of a sulfurated derivative of formula II$_e$ on the amide of formula II$_d$ is carried out, for example, by putting the amide of formula II$_d$ in solution in a solvent such as an alcohol like ethanol or methanol, then the successive addition of a base such as triethylamine and of the compound of the formula II$_e$ preferably with stirring at ambient temperature. The cyclization reaction of the compound of formula II$_f$ can be carried out in a solvent such as dichloromethane, dichloroethane or also chloroform and the reaction can be carried out in the presence of phosphorous pentachloride dissolved in dichloromethane at a temperature of approximately −78° C. in the presence of a base such as pyridine or dimethylaminopyridine. The reaction can be carried out with stirring at ambient temperature.

The product of formula II can be subjected to one or more of the reactions indicated above, these reactions being carried out under the same conditions as those defined above for the products of formula I. The compound of formula II$_a$ can be, for example, ethylisonitrosocyanoacetate which can be found in the form of a product marketed by LANCASTER under the reference 8930.

The compound of formula III as defined above can be obtained by reacting the compound in equilibrium in its trimer form of the formula

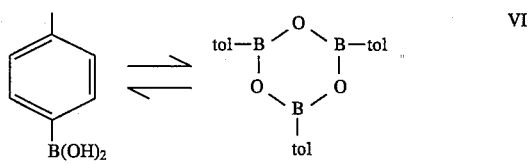

VI in which:

B is defined as above and tol is tolyl with an appropriate alcohol such as methanol, ethanol or butanol, or a diol such as propanediol, ethyleneglycol or dimethylpropanediol to obtain a compound of the formula

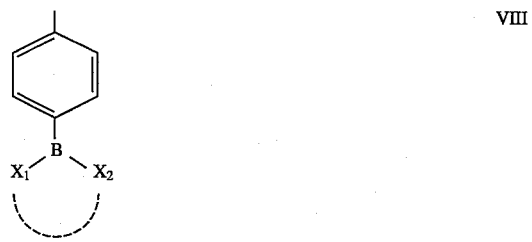

VIII in which B, $X_1$ and $X_2$ have the meanings above, and reacting the latter with a halogenation agent to obtain the product of formula III.

A modification of the process for the preparation of a compound of formula I comprises reacting a compound of formula IV with a halogenation reagent as taught by Snyder et al, J. Ann. Chem. Soc., Vol. 80, p. 835 (1958) to obtain a compound in equilibrium with its trimer of the formula

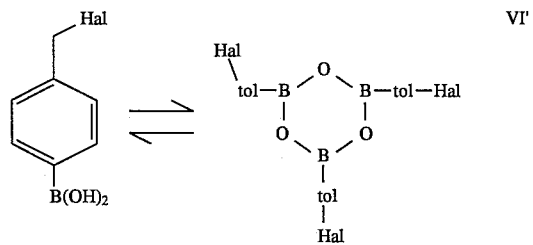

VI' in which B and tol have the meanings above, and Hal is halogen, preferably bromine, and reacting the latter with the compound of formula II to obtain the product of formula IV, then the synthesis is continued as indicated above to obtain the product of formula I. Such reactions can be carried out under the conditions indicated above and as described hereafter in the examples.

The preparation of the products of formula I can be effected by reacting a product of the formula

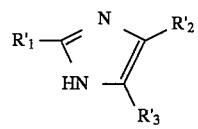

II in which $R'_1$, $R'_2$ and $R'_3$ have the meanings above with the product of formula III corresponding to the formula

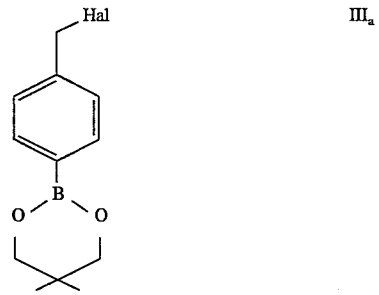

III$_a$ in which Hal and B have the meanings above to obtain the product of the formula IV corresponding to the formula

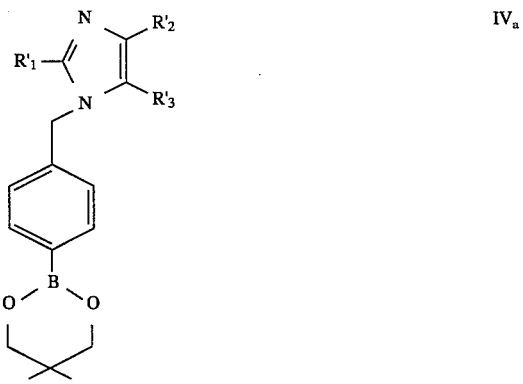

IV$_a$ in which $R'_1$, $R'_2$, $R'_3$ and B have the meanings above and reacting the latter with a compound of the formula

V$_a$ in which Hal and $R'_4$ have the meanings above. An example of such a preparation of a product of formula I is given in Example 1.

In the above process, the product of formula II can be reacted with the product of formula III corresponding to the formula

III$_b$ in which Hal and B have the meanings above to obtain a product of formula IV corresponding to the formula

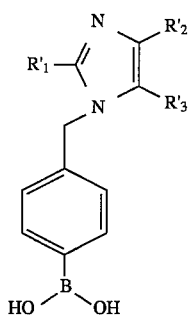

IV$_b$ or

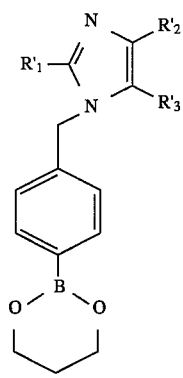

IV'$_b$ in which R'$_1$, R'$_2$, R'$_3$ and B have the meanings above and reacting the latter with a product of formula V. An example of such a preparation of a product of formula I is given in Example 2.

The product of formula I can be subjected, if necessary and if desired, to various reactions to give other products of formula I, as indiciated above, notably to a saponification reaction. Similarly, the products of formula IV and as an example, the products of formulae IV$_a$, IV$_b$ or IV'$_b$ can also be subjected to various reactions to give other products of formula IV.

A subject of the present invention is also new industrial products useful as intermediate products which are necessary for the preparation for the products of formula I which are the compounds of formulae IV and V as defined above.

Some products of formula III are also new and as such constitute a subject of the invention. These are -2-iodobenzene-sulfonamide
-2-iodo-N-[(propylamino)-carbonyl]-benzene-sulfonamide
-2-[4-(bromomethyl)-phenyl]-5,5-dimethyl-1,3,2-dioxaborolane
-2-[4-(bromomethyl)-phenyl]-1,3,2-dioxaborolane
-ethyl 1-[(4-boronophenyl)-methyl]-2-butyl-4-(methylthio)-1H-imidazole-5-carboxylate
-ethyl 2-butyl-1-[4-(5,5-dimethyl-1,3,2-dioxaborolan-2-yl)-benzyl]-4-(methylthio)-1H-imidazole-5-carboxylate
-ethyl-2-butyl-1-[4-(1,3,2-dioxaborolan-2-yl)-benzyl-4-(methylthio)-1H-imidazole-5-carboxylate
-(T-4)-((4-((2-butyl-4-(methylthio)-5-(ethoxycarbonyl)-1H-imidazole-1-yl-((methyl)-phenyl)-((2,2'-methylimino)-bis-((ethanolato))-(2-)-N,O,O')-boron
-ethyl 2-butyl-1-(4-(1,3,2-benzodioxaborol-2-yl)-benzyl-4-(methylthio)-1H-imidazole-5-carboxylate
-ethyl 2-butyl-1-(4-(4,4,5,5-tetramethyl-1,3,2-dioxolaborolan-2-yl)-benzyl)-4-(methylthio)-1H-imidazole-5-carboxylate
-ethyl 2-butyl-1-(4-(1,3,2-dioxolaborolan-2-yl)-benzyl-4-(methylthio)-1H-imidazole-5-carboxylate.

These products correspond to the following products 1 to 9:

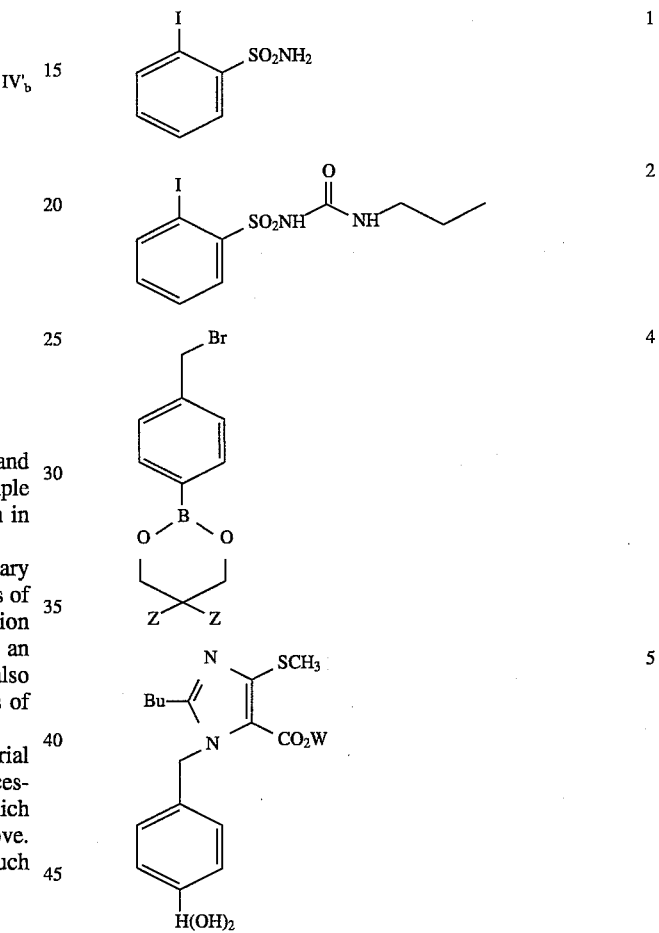

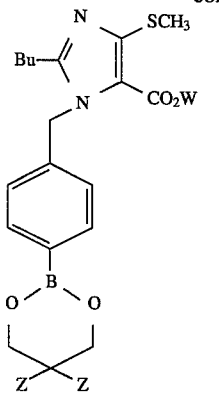

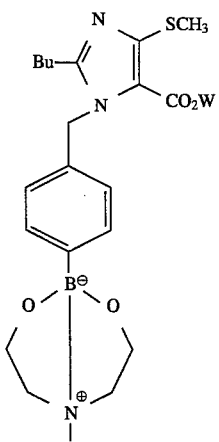

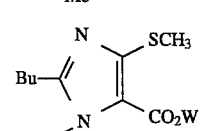

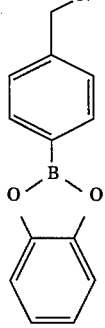

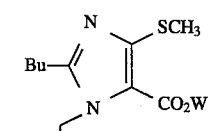

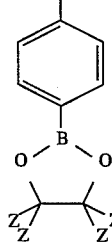

in which Z and W are individually hydrogen or alkyl notably methyl or ethyl and the products 4, 6 and 9 as defined above are called 4a, 6a and 9a respectively when A is methyl and 4b, 6b and 9b respectively when Z is hydrogen. Preparation methods for the above compounds and some of their homologs are described in the examples.

In the following examples, there are described several preferred embodiments to illustrate the invention. However, it is to be understood that the invention is not intended to be limited to the specific embodiments.

Preparation 1

2-iodobenzene-sulfonamide (product 1)

3.5 g of α-aminobenzene-sulfonamide and 25 ml of 98% concentrated sulfuric acid were heated at 60° C. and 20 g of ice were added. A solution of 1.45 g of sodium nitrite in 4 ml of water was added at 0°–5° C. and the mixture was stirred for 3 hours at a temperature below 10° C. Then a solution of 3.75 g of potassium iodide in 25 ml of water was added at 5°–10° C. and the reaction medium was stirred for 19 hours, 50 ml of water were added followed by filtering, washing with water, then taking up in 50 ml of ethyl acetate, washing with 0.2N solution of sodium thiosulfate, then with water, and concentrating to obtain 4 g of the expected product melting at 197°–198° C.

IR (nujol) 3360, 3255, 1562 cm$^{-1}$ Mass spectrum M$^+$ 283 NMR: CDCl$_3$ 5.17 (sl, N$\underline{H}_2$); 7.23 and 7.52 (td, aromatics, 2H); 8.08 and 8.20 (dd, aromatics, 2H)

Preparation 2

2-iodo-N-[(propylamino)-carbonyl]-1-benzene-sulfonamide (product 2)

4 g of iodobenzene-sulfonamide and 40 ml of acetone were mixed together and 3.92 g of potassium carbonate were added. The reaction was heated to reflux and 1.46 ml of n-propyl isocyanate were added. The medium was maintained at reflux for 2 hours, and after concentrating, 200 ml of water were added. Then, while cooling the reaction mixture to approximately 0°–5° C., a 2N hydrochloric acid solution was added until a pH of 3 was obtained. After crystallizing from acetone-isopropyl ether, 4.9 g of the expected product melting at 211°–212° C. were obtained.

IR (nujol) 3406, 3368, 1715, 1565, 1539 cm$^{-1}$ Mass spectrum M$^+$ 368 NMR: CDCl$_3$ 0.82 (tJ=7.5, C$\underline{H}_3$, 3H); 1.45 (m, C$\underline{H}_2$, 2H); 3.14 (m, C$\underline{H}_2$, 2H); 6.39 (t, CON$\underline{H}$, 1H); 7.29 (dt, J-1.5, aromatics); 7.54 (td, J-8.15, aromatics); 8.13 (m, aromatics); 7.59 (s, SO$_2$N$\underline{H}$, 1H).

The preparation of products 6a, 6b, 7, 8, 9a and 9b described in the experimental part can be schematized as indicated hereafter.

SCHEMA I

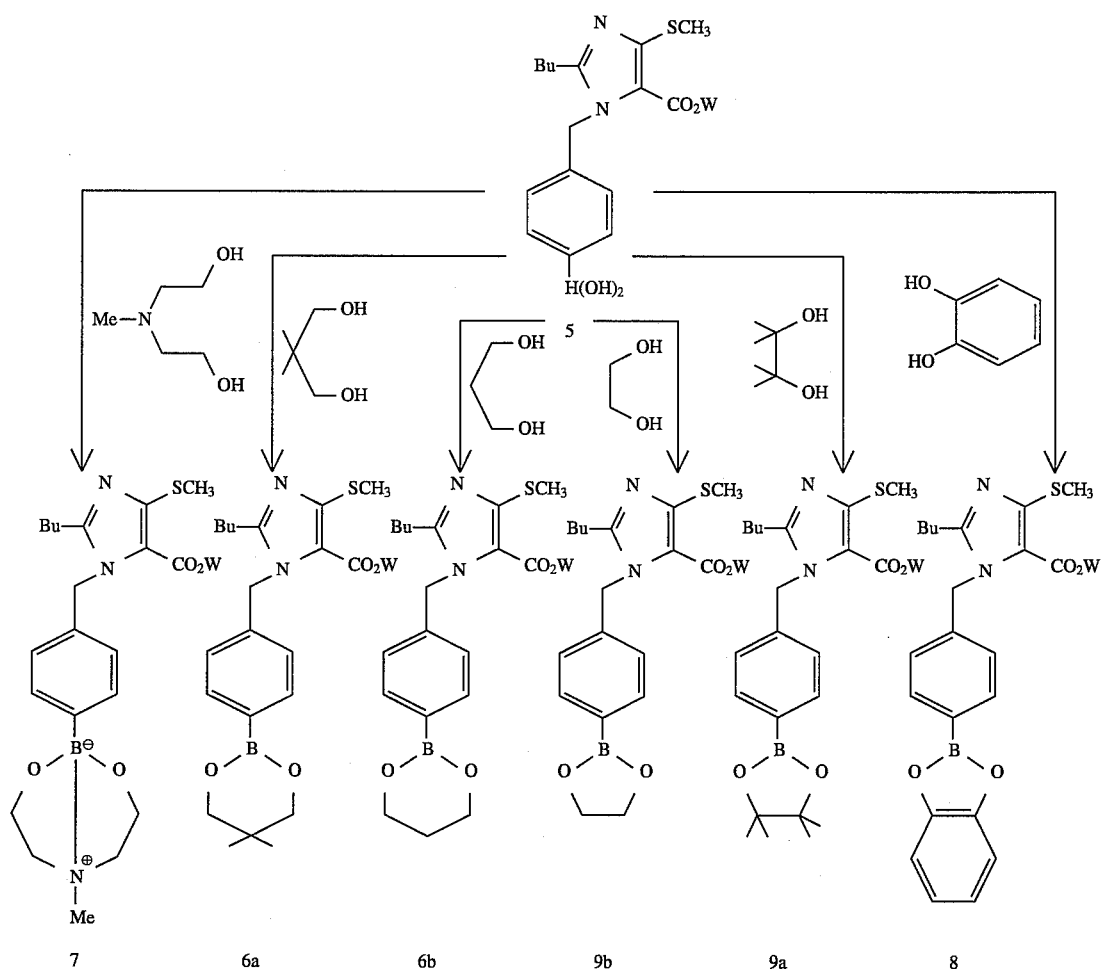

Preparation 3 ethyl 1-[(4-boronophenyl)-methyl]-2-butyl-4-(methylthio)-1H-imidazole-5-carboxylate (product 5)

Method 1

0.423 g of 4-bromomethyl-phenyl-boronic acid (prepared by the method described by Snyder et al., JACS, Vol. 80, p. 835 (1958)) were added to a mixture of 0.484 g of ethyl 2-butyl-4-(methylthio)-1H-imidazole-5-carboxylate, 5 ml of dimethylformamide and 0.552 g of potassium carbonate. After 48 hours of stirring at ambient temperature, the reaction mixture was poured into ice-cooled water. The reaction medium was stirred for 15 minutes followed by filtering, washing with water and crystallization from a mixture of cyclohexane and isopropyl ether to obtain 0.450 g of the expected product.

Method 2

A solution of 11 g of 2-(4-bromomethyl-phenyl)-1,3,2-dioxaborolane in 66 ml of dimethylformamide was added to a mixture of 9.44 g of ethyl 2-butyl-4-(methylthio)-1H-imidazole-5-carboxylate, 62 ml of anhydrous dimethylformamide and 10.78 g of potassium carbonate. After 48 hours of stirring at ambient temperature, the reaction mixture was poured into ice-cooled water and acidified to a pH of 2 with 2N hydrochloric acid. After filtering, washing with water and drying, 10.45 g of the expected product melting at 169°–170° C. were obtained.

IR (nujol) 1693, 1610, 1555, 1513 cm$^{-1}$ Mass spectrum 1074 (trimer form) NMR: CDCl$_3$ A mixture of resolved monomer and trimer approx. ¾–¼ of 0.87 and 0.86 signals (t, $\underline{CH_3}$, 3H); 1.32 (m, $\underline{CH_2}$, 2H); 1.30 (t, CO$_2$CH$_2$$\underline{CH_3}$, 3H); 1.64 (m, $\underline{CH_2}$, 2H); 2.60 (m, $\underline{CH_2}$, 2H); 2.61 and 2.63 (s, S$\underline{CH_3}$, 3H) 4.25 (q resolved, CO$_2\underline{CH_2}$CH$_3$, 2H); 5.55 and 5.60 (s, N—$\underline{CH_2}$-Ph, 2H); 7.00 and 7.68 (dl, aromatics, 2H); 7.11 and 8.12 (dl, aromatics, 2H); 4.93 (m, wide approx. 0.2H, mobile).

Preparation 4 ethyl 2-butyl-1-[4-(1,3,2-dioxaborolan-2-yl)-benzyl]-4-(methylthio)-1H-imidazole-5-carboxylate (product 6b)

A mixture of 1.292 g of ethyl 1-[(4-boronophenyl)-methyl]-2-butyl-4-(methylthio)-1H-imidazole-5-carboxylate of Preparation 3, 25 ml of toluene and 0.710 ml of 1,3 propanediol was stirred at reflux for 4 hours while eliminating the water formed. After evaporating to dryness under reduced pressure, the residue was crystallized hot and cold from heptane, filtered and washed to obtain 1.12 g of the desired product.

NMR: CDCl$_3$ (250 MHz) ppm 0.86 (t, 3H): CH$_3$ nBu; 1.30 (m, 2H)-1.60 (m, 2H)-2.58 (t, 2H): the CH$_2$ nBu's; 1.28

(t, 3H)-4.23 (q, 2H): —COOEt; 2.04 (m, 2H): O—CH$_2$—CH$_2$—CH$_2$—O; 4.14 (t, 4H): —O—CH$_2$—CH$_2$—CH$_2$—O—; 2.58 (s, 3H): SCH$_3$; 5.52 (s, 2H): Ar—CH$_2$-imidazole; 6.94 and 7.68 (2D, 4H): aromatics.

Preparation 5 ethyl 2-butyl-1-[4-(5,5-dimethyl-1,3,2-dioxaborolan-2-yl)-benzyl]-4-(methylthio)-1H-imidazole-5-carboxylate (product 6a)

Using the procedure of Preparation 4, 250 mg of ethyl 1-[(4-boronophenyl)-methyl]-2-butyl-4-(methylthio)-1H-imidazole-5-carboxylate and 70 mg of 2,2'-dimethyl 1,3-propanediol were reacted to obtain 200 mg of the desired product.

Preparation 6

(T-4)-((4-((2-butyl-4-(methylthio)-5-(ethoxycarbonyl)-1H-imidazol-1-yl)-methyl)-phenyl)-((2,2'-(methylthio)-bis-(ethanolato))-(2-)-N,O,O')-boron (product 7)

Using the procedure of Preparation 4, 2 g of ethyl 1-[(4-boronophenyl)-methyl]-2-butyl-4-(methylthio)-1H-imidazole-5-carboxylate, 30 ml of cyclohexane and 10 ml of ethyl acetate and then after hot dissolution, 0.611 ml of N-methyldiethanolamine were reacted to obtain after concentration, 2.17 g of the desired product.

NMR: CDCl$_3$ (250 MHz) ppm 0.85 (t, 3H): CH$_3$ nBu; 1.3 (t, 3H): CH$_3$ of —COOEt; 1.3 (m, 2H)-1.62 (q, 2H): CH$_2$ in position 3 and CH$_2$ in position 2 nBu; 2.30 (s, 3H): —N$^+$—CH$_3$; 2.60 (s, 2H and t, 2H): S—CH$_3$ and CH$_2$ in position 1 nBu; 2.98 and 3.20 (m, 4H): CH$_2$—N$^+$=; 4.15 (m, 4H): CH$_2$—B$^-$=; 4.27 (q, 2H): CH$_2$ of COOEt; 5.50 (s, 2H): Ar—CH$_2$-imidazole; 6.9 and 7.5 (2d, 4H) aromatics.

Preparation 7 ethyl 2-butyl-1-((4-1,3,2-benzodioxaborol-2-yl)-benzyl)-4-(methylthio)-1H-imidazole-5-carboxylate (product 8)

Using the procedure of Preparation 4, 1 g of ethyl 1-[(4-boronophenyl)-methyl]-2-butyl-4-(methylthio)-1H-imidazole-5-carboxylate and 0.293 g of catechol were reacted to obtain the desired product.

NMR: CDCl$_3$ (200 MHz) ppm 0.87 (t, 3H): CH$_3$ of nBu; 1.35 (m, 2H): CH$_2$ in position 3 of nBu; 1.65 (m, 2H): CH$_2$ in position 2 of nBu; 2.63 (t, 2H): CH$_2$ in position 1 of nBu; 1.30 (t, 3H): CH$_3$ of CO$_2$Et; 4.25 (q, 2H): CH$_2$ or CO$_2$Et; 2.63 (s, 3H): SCH$_3$; 5.6 (s, 2H): CH$_2$ benzyl; 7.1 and 8.05 (2d): aromatics; 7.15 and 7.3: catechol.

Preparation 8 ethyl 2-butyl-1-(4-(4,4,5,5-tetramethyl-1,3,2-dioxolaborolan-2-yl)-benzyl-4-(methylthio)-1H-imidazole-5-carboxylate (product 9a)

Using the procedure of Preparation 4, 0.5 g of ethyl 1-[(4-boronophenyl)-methyl]-2-butyl-4-(methylthio)-1H-imidazole-5-carboxylate and 0.189 g of pinacol were reacted to obtain 0.511 g of the desired product.

NMR: CDCl$_3$ (250 MHz) ppm 0.87 (t, 3H): CH$_3$ of nBu; 1.33 (m, 2H): CH$_2$ in position 3 of nBu; 1.63 (m, 2H): CH$_2$ in position 2 of nBu; 2.53 (t, 2H): CH$_2$ in position 1 of nBu; 1.33 (s, 12H): 4 CH$_3$—C—; 1.23 (t, 3H): CO$_2$Et; 4.23 (q, 2H): CO$_2$Et; 2.61 (s, 3H): S—CH$_3$; 5.53 (s): N—CH$_2$—Ar; 6.37 and 7.73 (2d, 4H): aromatics.

Preparation 9 ethyl 2-butyl-1-(4-(1,3,2-dioxolaborolan-2-yl)-benzyl-4-(methylthio)-1H-imidazole-5-carboxylate (product 9b)

Using the procedure of Preparation 4, 0.2 g of ethyl 1-[(4-boronophenyl)-methyl]-2-butyl-4-(methylthio)-1H-imidazole-5-carboxylate and 99 mg of ethylene glycol were reacted to obtain 0.21 g of the expected product.

NMR: CDCl$_3$ (200 MHz) ppm 0.9 (t, 3H): CH$_3$ of nBu: 1.35 (m, 2H): CH$_2$ in position 3 of nBu; 1.65 (m, 2H): CH$_2$ in position 2 of nBu; 2.63 (t, 2H): CH$_2$ in position 1 of nBu; 1.30 (t, 3H): CO$_2$Et; 4.25 (q, 2H): CO$_2$Et; 2.63 (s, 3H): S—CH$_3$; 5.60 (s, 2H): Ar—CH$_2$-imidazole; 4.45 (s, 4H): 2CH$_2$—O; 7.02 and 7.8 (2d); aromatics.

Preparation 10

2-bromo-N-[(propylamino)-carbonyl]-benzene-sulfonamide 15 g of 2-bromobenzene-sulfonamide in 150 ml of acetone were heated at reflux and 17.6 g of potassium carbonate were added. Then, 6.6 ml of N-propylisocyanate were added, followed by stirring for 2 hours and 30 minutes under reflux. The mixture was cooled to 0° C. and acidified to pH 5 to obtain 18.35 g of the expected product melting at 218°–219° C.

NMR: CDCl$_3$ ppm 0.84 (t, 3H): CH$_3$; 1.45 (m, 2H), 3.07 (q, 2H): the CH$_2$'s; 6.08 (l, 1H): NH; 7.5 (m, 2H), 7.71 (dd, 1H), 8.25 (dd, 1H): aromatics; 10.00 (l, 1H): NH.

EXAMPLE 1

2-butyl-4H-(methylthio)-1-[[2'-((((propylamino)-carbonyl)-amino)-sulfonyl)-1,1'(biphenyl)-4-yl]-methyl]-1H-imidazole-5-carboxylic acid di-potassium salt Stage A: 2-[(4-bromomethyl)-phenyl]-5,5-dimethyl-1,3,2-dioxaborolane 3.4 g of 4-methyl-phenyl-boronic acid (or its trimer form) and 2.6 g of 2,2-dimethyl-propane-1,3-diol in 50 ml of cyclohexane were refluxed for 4 hours while eliminating the water formed. 4.45 g of N-bromosuccinimide and 100 mg of azobisisobutyronitrile were added and the reaction medium was refluxed for 4 hours, cooled, filtered and washed with cyclohexane to obtain 7 g of the desired product melting at 110° C.

NMR: CDCl$_3$ ppm 1.01 (s, 6H): (CH$_3$)$_2$—C; 3.75 (s, 4H): CH$_2$—O—B; 4.52 (s, 2H): CH$_2$Br; 6.95 (d, 2H), 7,72 (d, 2H): aromatics.

Stage B: ethyl 2-butyl-1-[4-(5,5-dimethyl-1,3,2-dioxaborolan-2-yl)-benzyl]-4-(methylthio)-1H-imidazole-5-carboxylate A mixture of -g of ethyl 2-butyl-4-(methylthio)-1H-imidazole-5-carboxylate, 65 ml of dimethylformamide and 3.75 g of potassium carbonate was stirred for 30 minutes and then 8 g of the product of Stage A in solution in 32 ml of dimethylformamide were added. The reaction mixture was stirred for 48 hours at ambient temperature followed by pouring into water, extracting with ethyl acetate, drying and evaporating to dryness under reduced pressure. After impasting in a mixture of cyclohexane—ethyl acetate (8-2), 5.67 g of the desired product melting at 145°–146° C. were obtained.

NMR: CDCl$_3$ ppm 0.86 (t, 3H): CH$_3$ of nBu; 1.29 (t, 3H): CH$_3$ of CO$_2$Et; 1.34 (m, 2H), 1.62 (m, 2H), 2.60 (d, 2H): the CH$_2$'s of nBu; 2.6 (s, 3H): S—CH$_3$; 4.23 (q, 2H): CH$_2$ of CO$_2$Et; 5.52 (s, 2H): benzyl CH$_2$; 6.96 (d, 2H) and 7.71 (d, 2H): aromatics.

Stage C: ethyl 2-butyl-4H-(methylthio)-1-[[2'((((propylamino)-carbonyl)-amino)-sulfonyl)-1,1'(biphenyl)-4-yl]-methyl]-1H-imidazole-5-carboxylate A mixture of 62 mg of 2-bromo N-[(propylamino)-carbonyl]-benzene-sulfonamide, obtained by Preparation 10, 4 ml of toluene, 0.193 ml of a 2N solution of sodium carbonate in water, 7 mg of tetrakis (triphenylphosphine) palladium, 1.6 ml of ethanol and 85.5 mg of the product of Stage B and 0.4 ml of toluene was stirred for 24 hours at reflux. A little toluene was added and the reaction medium was acidified to a pH of 2 with 2N hydrochloric acid. Extraction was carried out with methylene chloride, followed by washing with water, drying and evaporating to dryness to obtain 165 mg of product which was chromatographed on silica eluting with a toluene-dioxane-acetic acid mixture (95-4-1) to obtain 75 mg of the desired product melting at 182° C.

NMR: CDCl$_3$ ppm 0.72 (t, 3H): CH$_3$ of nBu; 1.67 (m, 2H): CH$_2$; 3.03 (q, 2H): C$\underline{H}_2$—NH; 6.01 (s, 1H): SO$_2$N$\underline{H}$; 6.11 (t, 1H): CON$\underline{H}$; 7.25 (d), 7.64 (t), 7.53 (t), 8.12 (d): aromatics.

Stage D: 2-butyl-4H-(methylthio)-1-[[2'-((((propylamino)-carbonyl)-amino)-sulfonyl)-1,1'(biphenyl)-4-yl]-methyl]-1H-imidazole-5-carboxylic acid di-potassium salt 2.3 ml of a 6N solution of potassium hydroxide were added at 0° C. to a solution of 2 g of the product of Stage C in 40 ml of ethanol and the reaction medium was allowed to return to ambient temperature. After 72 hours, the precipitate was separated and washed with 4 ml of ethanol, then with 4 ml of ethyl acetate. After drying, 2.04 g of the desired product melting at >260° C. were obtained.

Analysis: C$_{26}$H$_{30}$K$_2$N$_4$O$_5$S$_2$

|  | % C | % H | % N | % S |
|---|---|---|---|---|
| calculated | 50.30 | 4.8 | 9.02 | 10.33 |
| found | 50.5 | 4.9 | 9.0 | 10.3 |

EXAMPLE 2a 2-butyl-4H-(methylthio)-1-[[2'-((((propylamino)-carbonyl)-amino)-sulfonyl)-1,1'(biphenyl)-4-yl]-methyl]-1H-imidazole-5-carboxylic acid di-potassium salt Stage A: 2-[(4-bromomethyl)-phenyl]-1,3,2-dioxaborolane Using the procedure of Stage A of Example 1, 21.06 g of 4-methyl-phenyl-boronic acid. 17.4 ml of trimethylene glycol, 250 ml of cyclohexane, 440 mg of azabis isobutyronitrile and 32.03 g of N-bromosuccinimide were reacted to obtain 31 g of the desired product melting at 108°–109° C.

NMR (CDCl$_3$) ppm 2.05 (m, 2H): central CH$_2$; 4.14 (t, 4H): B—O—C$\underline{H}_2$; 4.49 (s, 2H): C$\underline{H}_2$—Br; 7.27 (d, 2H) and 7.74 (d, 2H): aromatics.

Stage B: ethyl 2-butyl-1-[4-(1,3,2-dioxaborolan-2-yl)-benzyl]-4-(methylthio)-1H-imidazole-5-carboxylate A mixture of 34.5 g of ethyl 2-butyl-4-(methylthio)-1H-imidazole-5-carboxylate, 59 g of potassium carbonate, 3.82 g of tetrabutylammonium bromide and 312 ml of acetone was stirred for 30 minutes at 20°–22° C. Then, 33.6 g of the product of Stage A were added and the reaction medium was stirred for 24 hours, filtered and concentrated to dryness under reduced pressure. After crystallization both hot and cold from 59 ml of ethanol, 20.3 g of the desired product melting at 120°–121° C. were obtained.

NMR (CDCl$_3$) ppm 0.86 (t, 3H): CH$_3$; 1.28 (t, 3H): CH$_3$ of CO$_2$Et; 1.30 (m, 2H): CH$_2$; 1.60 (m, 2H): CH$_2$; 2.58 (t, 2H): C$\underline{H}_2$—C=N; 2.5 (s, 3H): S—CH$_3$; 2.04 (m, 2H): central CH$_2$; 4.14 (t, 4H): BO—CH$_2$; 4.23 (t, 2H): CH$_2$ of CO$_2$Et; 5.52 (s, 2H): C$\underline{H}_2$—N: 6.94 (d, 2H) and 7.68 (d, 2H): aromatics.

Stage C: ethyl 2-butyl-4H-(methylthio)-1-[[2'((((propylamino)-carbonyl)-amino)-sulfonyl)-1,1'(biphenyl)-4-yl]-methyl]-1H-imidazole-5-carboxylate 12.9 mg of triphenylphosphine and 5.5 mg of palladium acetate were added to a mixture of 264 mg of the product of Preparation 10 with 1.3 ml of toluene, 1.027 ml of a 2N solution of sodium carbonate, 97.8 mg of potassium bromide and 17.3 mg of galvinoxyl which had been stirred for 15 minutes. The mixture was stirred for 15 minutes and a solution of 400 mg of the product of Stage B in 1.3 ml toluene and 5.3 ml of ethanol was added. The mixture was stirred for 24 hours at reflux. After dilution with toluene and acidification by the addition of 1.47 ml of 2N hydrochloric acid, extraction was carried out with methylene chloride, followed by drying and evaporating to dryness under reduced pressure. The residue was chromatographed on silica (eluant: cyclohexane/n-chlorobutane/isopropanol 75-25-5) to obtain 0.25 g of the desired product which was identical to the product of Stage C of Example 1.

Stage D: 2-butyl-4H-(methylthio)-1-[[2'((((propylamino)-carbonyl)-amino)-sulfonyl)-1,1'(biphenyl)-4-yl]-methyl]-1H-imidazole-5-carboxylic acid di-potassium salt Using the procedure of Stage D of Example 1, the desired product was obtained.

EXAMPLE 2b 2-butyl-4H-(methylthio)-1-[[2'-((((propylamino)-carbonyl)-amino)-sulfonyl)-1,1'(biphenyl)-4-yl]-methyl]-1H-imidazole-5-carboxylic acid di-potassium salt Using the procedure of Example 2a, 10.1 mg of 1,3 bis-diphenyl phosphinopropane was used in Stage C instead of 12.9 mg of triphenylphosphine to obtain 49.6 mg of the product of Stage C of Example 2a which was treated as indicated in Stage D of Example 1 to obtain the expected product.

EXAMPLE 3 ethyl 2-butyl-4H-(methylthio)-1-[[2'-((((propylamino)-carbonyl)-amino)-sulfonyl)-1,1'(biphenyl)-4-yl]-methyl]-1H-imidazole-5-carboxylate Using the procedure of Stage C of Example 1, 0.0824 g of 2-iodo-N-propylamino-carbonyl-benzene-sulfonamide of Preparation 2 and 109 mg of the product of Preparation 4 were reacted to obtain the expected product.

EXAMPLE 4 ethyl 2-butyl-4H-(methylthio)-1-[[2'-((((propylamino)-carbonyl)-amino)-sulfonyl)-1,1'-(biphenyl)-4-yl]-methyl]-1H-imidazole-5-carboxylate Using the procedure of Stage C of Example 2, 828 mg of 2-iodo-N-propylamino-carbonyl-sulfonamide and 1.2 g of the product of Preparation 5 were reacted to obtain 905 mg of the desired product.

EXAMPLE 5 ethyl 2-butyl-4H-(methylthio)-1-[[2'((((propylamino)-(sulfonyl)-1,1'(biphenyl)-4-yl]-methyl-1H-imidazole-5-carboxylate Using the procedure of Stage C of Example 1, 442 mg of the product of Preparation 6 and 264 mg of the product of Preparation 10 were reacted to obtain 152 mg of the desired product.

EXAMPLE 6 ethyl 2-butyl-1H-(methylthio)-1-[[2'-((((propylamino)-carbonyl)-amino)-sulfonyl)-1,1'(biphenyl)-4-yl]-methyl]-1H-imidazole-5-carboxylate Using the procedure of Stage C of Example 2, 1 g of the product of Preparation 3 and 722 mg of the product of Preparation 10 were reacted to obtain 646 mg of the desired product.

EXAMPLE 7 ethyl 2-butyl-4H-(methylthio)-1-[[2'-((((propylamino)-carbonyl)-amino)-sulfonyl)-1,1'(biphenyl)-4-yl]-methyl]1H-imidazole-5-carboxylate Using the procedure of Example 6, 1 g of the product of Preparation 3 and 828 mg of 2-iodo-N-[(propyl-amino)-carbonyl]-benzene-sulfonamide of Preparation 2 were reacted to obtain 571 mg of the desired product.

EXAMPLE 8 ethyl 2-butyl-4H-(methylthio)-[[2'-((((propylamino)-carbonyl)-amino)-sulfonyl)-1,1'(biphenyl)-4-yl]-methyl]-1H-imidazole-5-carboxylate Using the procedure of Stage C of Example 2, 432.8 mg of the product of Preparation 7 instead of the product of Stage B of Example 2 were reacted to obtain 121 mg of the expected product.

EXAMPLE 9 ethyl 2-butyl-4H-(methylthio)-1-[[2'((((propylamino)-carbonyl)-amino)-sulfonyl)-1,1'(biphenyl)-4-yl-]-methyl]-1H-imidazole-5-carboxylate Using the procedure of Stage C of Example 2, 387 mg of the product of Preparation 9 instead of product of Stage B of Example 2 were reacted to obtain 220.5 mg of the expected product.

EXAMPLE 10 ethyl 2-butyl-4H-(methylthio)-1-[[2'-((((propylamino)-carbonyl)-amino)-sulfonyl)-1,1'(biphenyl)-4-yl]-methyl]-1H-imidazole-5-carboxylate Using the procedure of Stage C of Example 2, 440 mg of the product of Preparation 8 instead of the product of Stage B of Example 2 were reacted to obtain 172 mg of the expected product.

EXAMPLE 11

Pharmaceutical Composition

Tablets were prepared containing 5 mg of the product of Example 1 and sufficient excipient of lactose, talc, starch, magnesium stearate for a tablet of 200 mg.

There can be mentioned the following products which can be obtained by the process as defined above which is a subject of the invention:

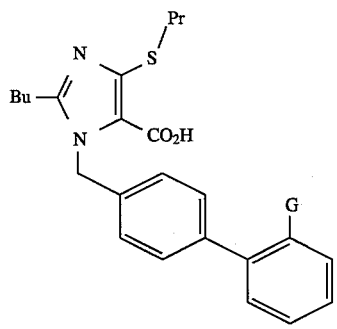

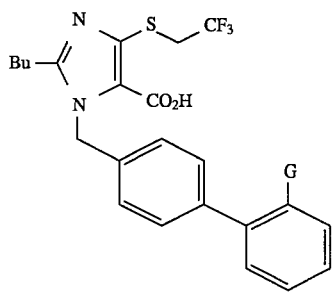

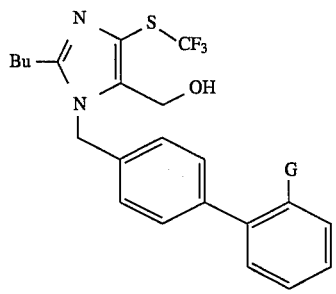

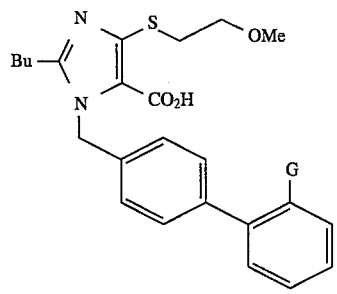

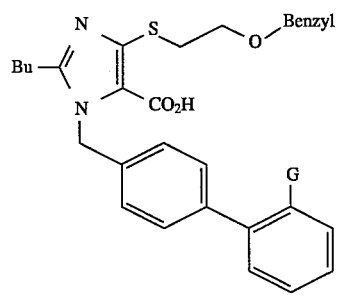

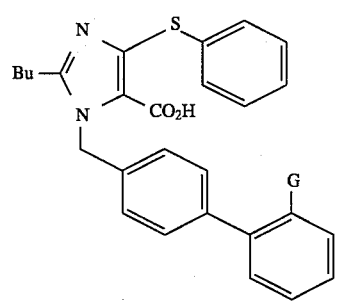

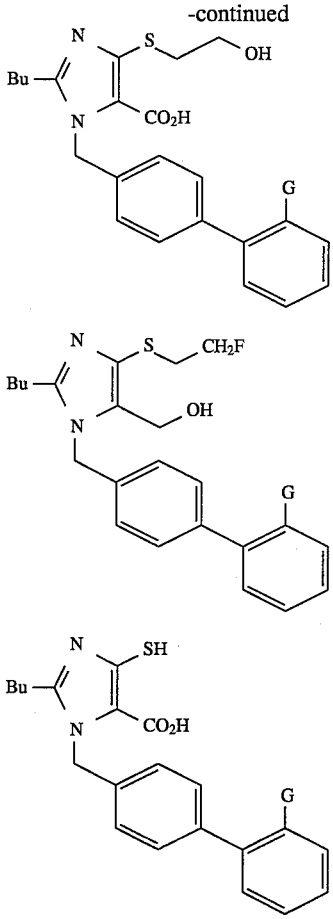

in which G preferably is —SO₂—NH—CO—NH—CH₂—CH₂—CH₃ or —SO₂—NH—CO₂ alkyl in which alkyl preferably is methyl, ethyl, propyl or butyl.

Various modifications of the process of the invention may be made without departing from the spirit or scope thereof and it is to be understood that the invention is intended to be limited only as defined in the appended claims.

What is claimed is:

1. A compound of the formula

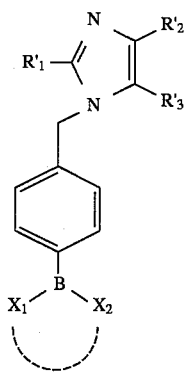

IV.

wherein $R'_1$ is selected from the group consisting of alkyl, alkenyl, alkynyl and alkylthio of up to 10 carbon atoms and cycloalkyl of 3 to 7 carbon atoms, all optionally substituted, $R'_2$ and $R'_3$ are individually selected from the group consisting of:

a) hydrogen, halogen, —OH, —SH, acyl of an organic carboxylic acid of 1 to 7 carbon atoms, —CN, free, salified or esterified carboxy and —PO₃(R)₂, b) —(CH₂)$_{m1}$—(SO)$_{m2}$—X—R₁₀, c) alkyl, alkenyl, alkoxy and optionally oxidized alkylthio of up to 6 carbon atoms optionally interrupted by at least one —O—, —S— or nitrogen and optionally substituted, d) optionally substituted phenyl, benzoyl and optionally oxidized phenylthio, e)

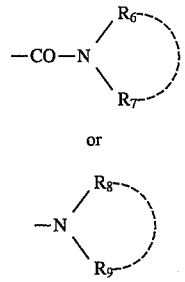

f) —S—S—R₁₂,

R is hydrogen or optionally substituted alkyl or phenyl, $m_1$ is an integer from 0 to 4, $m_2$ is an integer from 0 to 2, X is selected from the group consisting of a single bond, —NH—, —NHCO—, —NH—COO—, —N=CH—N—R₁₃ and —NHCONH—, R₁₀ and R₁₃ are individually selected from the group consisting of hydrogen, alkyl and alkenyl of up to 6 carbon atoms, cycloalkyl of 3 to 6 carbon atoms, optionally substituted phenyl and benzyl, pyridyl, nitropyridyl, pyrimidyl, tetrazolyl, diazolyl, piperidinyl, alkylpiperidinyl, thiazolyl, alkylthiazolyl, tetrahydrofuranyl and methyltetrahydrofuranyl; R₆ and R₇ or R₈ and R₉ are individually selected from the group consisting of hydrogen, amino acids, optionally substituted alkyl and alkenyl of up to 6 carbon atoms, optionally substituted phenyl, benzyl and phenethyl and —(CH₂)$_{m1}$—S(O)$_{m2}$—X—R₁₀ or R₆ and R₇ or R₈ and R₉ taken together with the nitrogen to which they are attached form a monocyclic ring of 5 to 7 ring members or condensed rings of 8 to 14 ring members, both optionally containing at least one heteroatom of the group consisting of —O—, —S— and nitrogen and optionally substituted with at least one member of the group consisting of halogen, —OH, —NO₂, alkyl and alkoxy of 1 to 6 carbon atoms, —NH₂, mono and dialkylamino of 1 to 6 carbon atoms and phenyl or R₈ and R₉ are individually acyl of an organic carboxylic acid of 1 to 6 carbon atoms or one of R₈ and R₉ is carbamoyl, alkoxycarbonyl or benzyloxycarbonyl or R₈ and R₉ together with the nitrogen form phthalimido or succinimido, R₁₂ has the definitions of R₂ and R₃ except for amino or alkoxy with the proviso at least one of R₂ and R₃ is an optionally substituted alkoxy or —(CH₂)$_{m1}$—S(O)$_{m2}$—X—R₁₀, B is boron and X₁ and X₂ are such that: either X₁ and X₂ are individually selected from the group consisting of hydroxyl, alkyl and alkoxy of 1 to 6 carbon atoms, phenyl and phenoxy, or X₁ with X₂ form with the boron atom to which they are linked a ring selected from the group consisting of

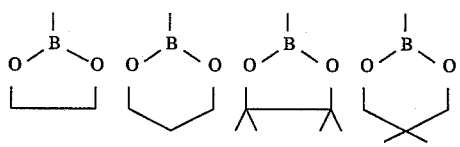

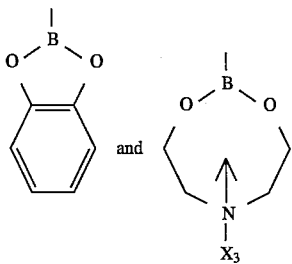

$X_3$ is hydrogen or alkyl of 1 to 4 carbon atoms and $X_4$ is halogen, alkoxy, triflate or —O—SO$_2$F with the reactive groups optionally protected.

2. Novel intermediates of claim 1 selected from the group consisting of ethyl 1-[(4-boronophenyl)-methyl]-2-butyl-4-(methylthio)-1H-imidazole-5-carboxylate, ethyl 2-butyl-1-[4-(5,5-dimethyl-1,3,2-dioxaborolan-2-yl)-benzyl]-4-(methylthio)-1H-imidazole-5-carboxylate, ethyl 2-butyl-1-[4-(1,3,2-dioxaborolan-2-yl)-benzyl]-4-(methylthio)-1H-imidazole-5-carboxylate, ((4-((2-butyl-4-(methylthio)-5-(ethoxycarbonyl)-1H-imidazole-1-yl-(methyl)-phenyl)-((2,2'-(methylimino)-bis-((ethanolato))-(2-)-N,O,O')-boron, ethyl 2-butyl-1-(4-(1,3,2-benzodioxaborol-2-yl)-benzyl)-4-(methylthio)-1H-imidazole-5-carboxylate, ethyl 2-butyl-1-(4-(4,4,5,5-tetramethyl-1,3,2-dioxolaborolan-2-yl)-benzyl)-4-(methylthio)-1H-imidazole-5-carboxylate and ethyl 2-butyl-1-(4-(1,3,2-dioxolaborolan-2-yl)-benzyl)-4-(methylthio)-1H-imidazole-5-carboxylate.

* * * * *